United States Patent [19]

Hytte et al.

[11] Patent Number: 5,656,281
[45] Date of Patent: Aug. 12, 1997

[54] WATER-DISPERSIBLE GRANULES OF PHOSPHITE FUNGICIDAL PRODUCTS

[75] Inventors: Jean-Michel Hytte, Lyon; Christian Segaud, Genas, both of France

[73] Assignee: Rhone-Poulenc Agrochimie, Lyon Cedex, France

[21] Appl. No.: 375,178

[22] Filed: Jan. 18, 1995

Related U.S. Application Data

[63] Continuation of Ser. No. 90,248, Jul. 9, 1993, abandoned, which is a continuation of Ser. No. 625,952, Dec. 11, 1990, abandoned.

Foreign Application Priority Data

Dec. 14, 1989 [FR] France ................... 89 16851

[51] Int. Cl.$^6$ ................ A01N 25/12; A01N 25/14
[52] U.S. Cl. ............ 424/408; 424/405; 424/409; 514/142
[58] Field of Search ............ 424/405, 408, 424/499, 501, 502, 409; 514/142; 71/DIG. 1

[56] References Cited

U.S. PATENT DOCUMENTS

| | | | |
|---|---|---|---|
| H811 | 8/1990 | Nasu et al. | 514/92 |
| 3,591,682 | 7/1971 | Thiolliere | 424/211 |
| 3,920,442 | 11/1975 | Albert et al. | 71/92 |
| 4,075,324 | 2/1978 | Thizy et al. | 424/128 |
| 4,139,616 | 2/1979 | Ducret et al. | 514/141 |
| 4,382,928 | 5/1983 | Abblard et al. | 424/211 |
| 4,542,023 | 9/1985 | Lacroix et al. | 514/126 |
| 4,936,901 | 6/1990 | Surgant, Sr. et al. | 71/92 |
| 4,994,495 | 2/1991 | Clough et al. | 514/574 |
| 5,001,150 | 3/1991 | Yap | 514/476 |
| 5,167,694 | 12/1992 | Robinson | 71/92 |

FOREIGN PATENT DOCUMENTS

| | | |
|---|---|---|
| 2589325 | 5/1987 | France . |
| 832306 | 3/1983 | Saudi Arabia . |
| 2131296 | 6/1984 | United Kingdom . |
| 2150027 | 6/1985 | United Kingdom . |
| 2163652 | 3/1986 | United Kingdom . |
| WO8900079 | 1/1989 | WIPO . |

OTHER PUBLICATIONS

CA 100 (1): 2186 +; Stable Compositions Based on Feuareinol . . . funguides; Barlet et al.
CA 103 (11): 83518 u; Stabilized Funguide . . . Product; Barlet et al.
Atlas In Agriculture, Water Dispersible Granules.
David Seaman, Trends in *Pesticide Formulation*, L'actualite Chimique, 58–61, Mar. 1988.
Rogiers, *New Formulation Trends in the Agricultural Industry*, Nov. 1988. (ICI Specialty Chemicals, Reprint RP 25/88E).
French Search Report for Appln. 89–16851.

*Primary Examiner*—John C. Bleutge
*Assistant Examiner*—Robert H. Harrison
*Attorney, Agent, or Firm*—Morgan & Finnegan, L.L.P.

[57] ABSTRACT

Concentrated fungicidal compositions, in the form of water-dispersible granules are disclosed which contain:

- 5 to 95% of phosphite-type active substance in solid or soildified form,
- 0.1 to 8% of a wetting agent,
- 0.3 to 15% of a dispersing agent,
- 0 to 50% of a support. These granules have a particle size of between 0.1 mm and 10 mm.

15 Claims, No Drawings

WATER-DISPERSIBLE GRANULES OF PHOSPHITE FUNGICIDAL PRODUCTS

This is a continuation of application Ser. No. 08/090,248, filed on Jul. 9, 1993, now abandoned, which is a continuation of application Ser. No. 07/625,952, filed on Dec. 11, 1990, now abandoned.

The present invention relates to novel improved formulations of compounds which have a fungicidal action, and, especially, based on phosphite-type derivatives, and to the use of these formulations for the fungicidal treatment of plants.

There is known a large number of phosphite-type compounds which can be used for combating fungal attacks of plants. Such compounds comprise phosphorous acid as well as its salts and its alkyl derivatives, and they are described, for example, in U.S. Pat. Nos. 4,075,324, 4,119,724, 4,139,616 and others.

More particularly, there may be cited, as phosphite-type compounds which can be used for combating fungal attacks of plants, besides phosphorous acid itself, as well as the ($C_1$-$C_4$)alkyl phosphorous acids and the alkali metal salts and/or alkaline earth metal salts and/or aluminium salts of these acids.

Although the use of such compounds has already been practised for a good number of years, the users have regularly encountered various technical difficulties.

It is an aim of the present invention to provide compositions or formulations which have improved properties.

It is therefore a particular aim of the present invention to provide compositions or formulations which produce little or no dust. Even if the active substance has a low toxicity, as is the case with the phosphite-type derivatives, the dusts are a source of pollution for the environment, both in the manufacture of the agrochemical formulations and when they are handled, transported, stored or used by the agriculturist.

It is another aim of the present invention to provide compositions or formulations which can be measured out with ease. Indeed, wettable powders, and especially micronised wettable powders, tend to have large differences in apparent density as the powders pack down, which leads to great difficulties if it is desired to measure out the products by volume.

It is another aim of the present invention to provide compositions or formulations which do not employ organic solvents, which is equally favorable from the point of view of nuisance and of the environment.

It is another aim of the present invention to provide compositions or formulations which can have, in practice, a truly high content of active substance.

It is another aim of the present invention to provide compositions or formulations which can contain a water-degradable active substance, which is not possible with other types of compositions, such as concentrated suspensions.

It is another aim of the present invention to provide compositions or formulations which can be handled with ease, which can flow easily like a liquid, which are easy to measure out by volume, and which leave no, or little, residues in the emptied packaging after use.

It is another aim of the present invention to provide compositions or formulations which are suitable for phosphite-type fungicides which have a hygroscopic character and/or are water-soluble. From amongst these derivatives, the purely inorganic derivatives of the phosphite type may be cited especially, that is to say phosphorous acid and its salts, and, more particularly, its alkali metal salts. The alkyl phosphite derivatives of alkali metals also present problems of the same type because they are hygroscopic. It is very difficult to make wettable powders with such compounds, precisely because of this hygroscopicity which leads to agglomeration of the solid fungicide particles between themselves, even to their transformation under the influence of atmospheric humidity into a more or less sticky liquid. When it is attempted to produce wettable powders, these phenomena cause caking, which has very annoying consequences from every point of views for the manufacturer, caking leads to fouling of the apparatus, even to choking up, obstructing and jamming the apparatus. For the agriculturist, caking leads to the fact that it is impossible to apply the products homogeneously, to choking up of the spraying equipment, and to the fact that the wettable powders dissolve unsatisfactorily in water, this unsatisfactory dissolution being accompanied by a lack of homogeneity in the resulting mixtures, which is also annoying insofar as this prevents the products from being applied at a homogeneous and constant concentration.

Apart from caking, the tendency of the solid particles to agglomerate also leads to a packing-down effect which makes the product unsuitable for storage.

In view of the problems caused by the high hygroscopicity of phosphite-type products, one could think that it might suffice to use these products in aqueous solutions or suspensions, but this is hardly possible since, with the aim of widening their spectrum of activity, these products are often used not by themselves but in the form of a combination with other active substances.

Other aims of the invention will emerge more clearly in the course of the description which will follow.

It has now been found that these aims can be achieved, completely or in part, with the aid of compositions according to the invention.

In the disclosure of the present invention, all percentages given are percentages by weight, unless indicated to the contrary. Moreover, the term "surface-active agent" is used to denote compounds known in the English language as "surfactants".

Furthermore, hereinafter the following definitions are used for the terms "wettability time", "dispersibility" and "suspendibility":

The wettability time is measured in accordance with Technique MT 53.3.1 described in the CIPAC HANDBOOK, volume 1, pages 966–967, edited by G. R. Raw in 1970. It consists essentially in measuring the wetting time of 5 g of granules poured onto 100 ml of water.

The dispersibility is measured in accordance with the following technique: 10 g of granules are poured into a 250 ml test tube which contains 250 ml of hard water defined in Method 18.1.4 described in the CIPAC HANDBOOK, volume 1, pages 875–878. The test tube and its contents are turned upside down 10 times, the contents are then poured onto a sieve of 160-microns mesh, and the residue is dried and weighed; the dispersibility is then expressed by the percentage of the granules which pass through the sieve.

The suspendibility is measured in accordance with Technique MT 15.1 note 4, described in the CIPAC HANDBOOK, volume 1, pages 861–865. It consists essentially in pouring 2.5 g of the granules into a 250 ml test tube which contains 250 ml of hard water, turning the test tube and its contents upside down 30 times, allowing everything to rest for 30 minutes, and measuring the mass of material contained in the bottom 25 ml of the test tube (10% of the test tube volume); the suspendibility is then expressed by the percentage of the matter which remains in suspension in the top 90% of the test tube.

The compositions according to the invention are characterised in that they are granules which contain:

5 to 95% of phosphite-type active substance in solid or solidified form. Solidified form is intended to mean that, if the active substance is in liquid form when it is in the pure state, it is then used in the invention in absorbed or adsorbed form on a solid support such as, for example, one of the supports defined hereinafter, in particular silica or diatomaceous earth.

0.1 to 8%, and preferably 0.5 to 5%, of a wetting agent, 0.3 to 15%, and preferably 2 to 8%, of a dispersing agent, 0 to 50% of a support or filler, these granules having a size between 0.1 mm and 10 mm, and preferably between 0.2 and 4 mm.

By the term wetting agent is meant a compound which permits the granule to rapidly penetrate into the water, and, more precisely, a compound which, when intimately mixed in proportions of 1% with either kaolin or atrazine, where these supports (atrazine or kaolin) have a granule size of between 5 and 50 microns, give a mixture which has a wettability time of less than 2 minutes. The test is usually carried out with kaolin when the wetting agent is capable of wetting a hydrophilic solid. Conversely, the test is carried out with atrazine when the wetting agent is capable of wetting a hydrophobic solid. This wetting agent can be an ionic or non-ionic agent or a mixture of such surface-active agents.

Compounds which are usable as wetting agents and which can be cited are, for example, the alkylarylsulphonate-type salts, in particular the alkali metal alkylnaphthalensulphonates, the salts of polycarboxylic acids, polycondensates of ethylene oxide with fatty alcohols or with fatty acids or with fatty amines, or substituted phenols (in particular alkylphenols or arylphenols), and salts of esters of sulphosuccinic acids.

By the term dispersing agent is meant a compound which ensures that the particles remain suspended in the application mixture and which allows rapid disintegration of the granule in the water. More precisely, by dispersing agent is meant a compound which, when intimately mixed in proportions of 5% with either kaolin or atrazine, these supports (atrazine or kaolin) having a granule size between 5 and 50 microns, gives a mixture which has a suspendibility of more than 70%. The test is usually carried out with kaolin when the dispersing agent is capable of dispersing a hydrophilic solid. Conversely, the test is carried out with atrazine when the dispersing agent is capable of dispersing a hydrophobic solid. The dispersing agent can be an ionic or non-ionic agent or a mixture of such surface-active agents.

As compounds which are suitable as dispersing agents there may be cited, for example, arylsulphonate-type polymers, in particular the alkali metal polynaphthalenesulphonates obtained by condensation of (alkyl) arylsulphonates with formaldehyde, the lignosulphonates, the polyphenylsulphonates, salts of polyacrylic acids, salts of lignosulphonic acids, salts of phenolsulphonic acids or naphthalenesulphonic acids, taurine derivatives (in particular alkyltaurates), phosphoric esters of alcohols or of polycondensates of ethylene oxide and phenols, esters of fatty acids and polyols, and the derivatives of the preceding compounds which have sulphate, sulphonate and phosphate functions.

The term "support" in the present disclosure refers to a solid organic or inorganic material, natural or synthetic, with which the active substance is combined so as to facilitate application to the plant or to the soil. This support is therefore generally inert and agriculturally acceptable, in particular on the treated plant. The support can be selected for example from amongst clay, diatomaceous earth, the natural or synthetic silicates, silica, resins, waxes, solid fertilizers, soluble or insoluble mineral salts, organic derivatives, and polysaccharide compounds such as starch, cellulose, sugars and lactose.

Preferred supports amongst those which are suitable are hydrophilic supports which have a disintegrating action, that is to say which facilitate the rupture of the granule according to the invention in the presence of water. As compounds of this type there may be mentioned the bentonites (natural or activated), starch and its derivatives (in particular the alkylstarches and the carboxyalkylstarches), the celluloses (in particular microcrystalline cellulose) and the derivatives of cellulose (in particular carboxyalkylcellulose), the alginates, soluble mineral salts, or reticulated polyvinylpyrrolidone.

Besides the fungicidal compounds of the phosphite type which have been mentioned above, the compositions according to the invention advantageously contain at least a second fungicidal compound (possibly three, or even more) of a type which differs from the first compound, which has the aim of widening the spectrum of the first one. As the second fungicide, there may be mentioned the contact fungicides, that is to say which act by contact with the plants, and, in particular, the contact fungicides which are solid and water-insoluble in the pure state. As compounds of this type, there may be mentioned the dithiocarbamates such as maneb, zineb, thiram (or thiuram) and mancozeb, the copper compounds which are active in agriculture, chlorothalonil, captafol, captan, folpet, and dithianone. As the second fungicide, cymoxanil or fenarimol, or a triazole- or acylalanine-type fungicide, can also be used.

This second fungicidal agent is found in the compositions according to the invention in amounts of between 0.1 and 95%, preferably between 10 and 50% (percentages based on the total granulated composition according to the invention). The first fungicidal compound according to the invention is therefore found in quantities of preferably between 20 and 60%.

Besides the above-described constituents, the compositions according to the invention can contain 0 to 30% of suitable additives, such as antifoams, sequestering agents, stabilisers, penetrating agents, adhesives, anti-caking agents, colorants, and others.

Besides the constituents indicated above, the compositions of the invention can contain other compounds, in particular compounds which have, more specifically, a binding action, that is to say a compound of the polymer type which helps cohesion and processing of the granules. These compounds with a binder action can either be compounds which are different from those cited above, or they can be the same compounds inasfar as they are capable of having a double action. As compounds or agents of this type, it is preferred to use agents such as gums, in particular gum arabic; glues, in particular dextrin; sugars, in particular glucose and lactose; cellulose derivatives, in particular alkylcellulose and carboxyalkylcellulose; starch; polymers, in particular polyvinylpyrrolidone, polyvinyl alcohol, polyethylene glycol, polyacrylate, vinyl polyacetates; and soluble waxes and alkali metal silicates.

The binding agent and the agent, or support, with disintegrating properties do not have contrary effects inasmuch as the action of the binding agent is exercised in the solid state, to bind together the different solid particles of the compositions according to the invention, and the action of the agent with disintegrating properties is exercised in the liquid state, when the compositions according to the invention are dispersed in water.

The compositions according to the invention can, of course, furthermore contain all the solid or liquid additives which correspond to customary formulation techniques.

From amongst the constituents of the granules according to the invention, it is also preferred to choose those which, by virtue of their nature and their dose in the compositions according to the invention, give granules with:
- a wettability time of less than 5 minutes, preferably less than 2 minutes (this wettability time being measured as shown before, but by direct measuring, without prior mixing with kaolin or with atrazine),
- a dispersibility of more than 85%, preferably more than 92% (this dispersibility being measured as shown above, but by directly measuring, without prior mixing with kaolin or atrazine),
- a suspendibility of more than 50%, preferably more than 70% (this suspendibility being measured as shown above, but by directly measuring, without prior mixing with kaolin or atrazine).

The preparation of the granules according to the invention is generally carried out starting with wettable powders which have the same chemical composition as the granules according to the invention, and then these wettable powders are moistened, shaped and finally dried.

To obtain wettable powders according to the invention, the active substance, or active substances, are intimately mixed in suitable mixers with additional substances, and, if appropriate, the porous vehicle is impregnated with them, and everything is ground on mills or other suitable grinders.

According to a first preparation method for the granules according to the invention, the wettable powders are moistened by directly adding liquid water (from 1 to 20% of water, preferably 10 to 18% of water), and this moistened powder, which has the consistency of a dough, is extruded through a grill or perforated plate in such a way as to obtain an extrudate in the form of a large number of elongated cylinders, which are sometimes named rolls or even spaghetti, which are subsequently broken up lengthwise in such a way as to produce a large number of small short cylinders which constitute the granules according to the invention. These are moist and only need drying (for example at more than 80° C., preferably at 100° C., in a ventilated atmosphere) to obtain proper granules according to the invention which can be marketed.

In a second preparation method for the granules according to the invention, the wettable powders are moistened by being sprayed with water (from 5 to 35% of water, preferably 20 to 30% of water) in a fluidised bed formed with the wettable powder. This operation leads directly to the formation of moist granules, and it is therefore only necessary to dry them to obtain the proper granules according to the invention which can be marketed.

According to a third preparation method for the granules according to the invention, the wettable powders are moistened by direct spraying of liquid water (from 1 to 20% of water, preferably 10 to 18% of water) onto the wettable powder which is located on an inclined and rotating plate. The fact that this plate rotates allows the powder grains to remain dissociated from one another. The spraying of water onto these grains during the movement also leads to the formation of moist granules which then only need drying (for example at more than 80° C., preferably at 100° C., in a ventilated atmosphere) so as to obtain the proper granules according to the invention which can be marketed.

According to a fourth preparation method for the granules according to the invention (named atomisation), a concentrated suspension is prepared from a wettable powder, by directly adding liquid water (from 20 to 70% of water, preferably 30 to 50% of water); this suspension is then sprayed in a dryer with hot air (atomiser) which allows fine and dry granules to be obtained by rapid evaporation of the water contained in the droplets of suspension; the temperature of the drying air is generally between 120° and 300° C., preferably between 150° and 250° C.

The "dispersible" granules are called in the English language "water-dispersible granules (WG)"; more exactly, they are granules which are readily dispersible in water.

The granules according to the invention are therefore concentrated compositions which are intended to be diluted by the agriculturalists in containers which contain water, so as to be able to apply these diluted mixtures. These diluted mixtures are usually applied at 50 to 1000 l/ha, preferably 100 to 500 l/ha, the active substance itself being applied at 0.4 to 2 kg/ha.

The invention also comprises a process for treating plants against fungal attacks, characterised in that a diluted mixture is applied which is obtained from concentrated granules as described in the above text.

The following examples which are given without any limitation being implied, illustrate the invention and demonstrate how it can work. The active substances introduced are of the "technical grade", as obtainable directly at the end of their manufacture. Parts are parts by weight.

EXAMPLES 1 TO 6

Intimate mixtures are prepared of the various following compositions:
Composition 1:
$K_2HPO_3$ 500 parts
Folpel 222 parts
Maleic anhydride/isobutylene condensate, in the form of the potassium salt (wetting agent) 30 parts
Sodium polyphenylsulphone sulphonate (dispersant) 60 parts
Kaolin . . . 188 parts
Composition 2:
$K_2HPO_3$ 335 parts
Copper oxychloride 439 parts
Sodium alkylnaphthalenesulphonate (wetting agent) 30 parts
Sodium alkylnaphthalenesulphonate/formol polycondensate (dispersant) 60 parts
Kaolin . . . 136 parts
Composition 3:
$K_2HPO_3$ 470 parts
Mancozeb 412 parts
Cymoxanil 31 parts
Sodium alkylnaphthalenesulphonate (wetting agent) 30 parts
Sodium alkylnaphthalenesulphonate/formol polycondensate (dispersant) 57 parts
Composition 4:
$K_2HPO_3$ 375 parts
Chlorothalonil 191 parts
Sodium alkylnaphthalenesulphonate (wetting agent) 30 parts
Sodium alkylnaphthalenesulphonate/formol polycondensate (dispersant) 60 parts
Kaolin . . . 344 parts
Composition 5:
$[C_2H_5O\text{—}PH(O)\text{—}]_3Al$ 800 parts 10:1 ethylene oxide/nonylphenol condensate (wetting agent) 20 parts
Sodium alkylnaphthalenesulphonate/formol polycondensate (dispersant) 35 parts
40:1 ethylene oxide/nonylphenol condensate (binder) 25 parts
Alkylpolysiloxane (antifoam) 5 parts
Bentonite (support with disintegrating properties) 40 parts
Kaolin (support) 75 parts
Composition 6:
[$C_2H_5O$—PH(O)—]$_3$Al 500 parts
Folpet 250 parts
Cymoxanil 40 parts
Sodium alkylnaphthalenesulphonate (wetting agent) 20 parts
40:1 ethylene oxide/tris(phenylethyl)phenol condensate (dispersant) 50 parts
Tridecyl alcohol (antifoam) 5 parts
Sodium lignosulphonate (dispersant and binder) 135 parts The intimate mixture of the constituents of these various compositions is obtained by passing them through a hammer mill which has a grating of 0.5 mm mesh for breaking up the lumps. In this way, a wettable powder is obtained which contains particles of a size between 5 and 50 microns.

The first of these compositions was shaped into granules by the extrusion technique described hereinabove. In a mixer/beater, 500 g of wettable powder are moistened with 15% of water for about 5 minutes. The powder is then continuously extruded with the aid of a perforated-roll extruder (openings of diameter: 1.5 mm). The moist granules which have thus been formed are dried in a fluidised bed in which the temperature of the air which enters is 100° C., and then the mixture is sieved in such a way as to obtain granules of a size of between 0.5 and 1.6 mm, on average of about 1.5 mm.

Compositions 2, 3 and 4 were shaped into granules by the fluidised-bed technique also described above. 500 g of homogenised wettable powder are fluidised in a fluidised-bed granulator. Agglomeration is obtained by spraying 25% of water onto the powder bed at ambient temperature. The granules formed are then dried by raising the temperature of the air which enters to 100° C., and then the mixture is sieved as above, and granules of a similar size are obtained.

Compositions 5 and 6 were shaped into granules by the atomisation technique also described above. 600 of wettable powder are dispersed in 400 g of water in such a way as to constitute a suspension which is sprayed in a jet atomiser where the temperature of the air at the inlet is 180° C. and the temperature of the air at the outlet is 90° C. Granules of a size between 0.1 and 0.4 mm are obtained.

By these various processes, granules are obtained whose wettability time ("WT"), dispersibility ("D") and suspendibility ("S") are determined, and these are listed in the table below.

Furthermore, these granules are preserved for one month at 50° C.: these granules preserve their physicochemical properties.

| Composition | 1 | 2 | 3 | 4 | 5 | 6 |
|---|---|---|---|---|---|---|
| WT (minutes) | 5 | 20 | 30 | 20 | 5 | 90 |
| D (percent) | 92 | 100 | 94 | 100 | 99 | 100 |
| S (percent) | 86 | 58 | 85 | 90 | 98 | 97 |

The above-described granules are mixed with water in a proportion of one kilogram of granules per liters of water. In this way, diluted mixtures are obtained which are sprayed at 300 l/ha onto grapevine which is infested with mildew: an excellent fungicidal activity is obtained.

We claim:
1. A concentrated fungicidal composition of water-dispersible consisting essentially of:
   5 to 95% of a fungicidal phosphite active substance in solid or solidified form,
   0.1 to 8% of a wetting agent,
   0.3 to 15% of a dispersing agent, and
   0 to 50% of a support,
   0 to 30% total of one or more additives selected from the group consisting of antifoaming agents, sequestering agents, stabilisers, penetrating agents, adhesives, anti-caking agents and colorants,
   these granules having a size of between 0.1 mm and 10 mm, and the composition has
   a. a wettability time of less than 5 minutes,
   b. a dispersibility of more than 92%, and
   c. a suspendability of more than 86%.
2. The composition according to claim 1, wherein the composition contains from 0.5 to 5% of the wetting agent.
3. The composition according to claim 1, wherein the composition contains from 2 to 8% of the dispersing agent.
4. The composition of claim 1, wherein the size of the granules is between 0.2 mm and 4 mm.
5. The composition according to claim 1, wherein the phosphite active substance has a hygroscopic character.
6. The composition of claim 1, wherein the phosphite active substance is water soluble.
7. The composition according to claim 1, wherein the phosphite active substance is phosphorous acid or one of its salts or a salt of an alkyl phosphorous acid.
8. The composition according to claim 1, wherein the wetting agent comprises a compound selected from the group consisting of alkylarylsulphonate-type salts, salts of polycarboxylic acids, polycondensates of ethylene oxide with fatty alcohols, fatty acids, fatty amines, the substituted phenols and the salts of esters of sulphosuccinic acids.
9. The composition according to claim 8, wherein the wetting agent comprises a compound from the group consisting of alkali metal alkylnaphthalenesulphonates, alkylphenols and arylphenols.
10. The composition according to claim 1, wherein the dispersing agent comprises an arylsulphone polymer, a lignosulphonate, a polyphenylsulphonate, a salt of polyacrylic acid, a salt of lignosulphonate, a salt of polyacrylic acid, a salt of lignosulphonic acid, a salt of phenolsulphonic acid, a salt of naphthalenesulphonic acid, a taurine, an alkyltaurate, a phosphoric ester of an alcohol, a phosphoric ester of a polycondensate of ethylene oxide and phenol, an ester of a fatty acid and a polyol, or a sulphate, sulphonate, or phosphate of the preceding compounds.
11. The composition according to claim 1, wherein the dispersing agent comprises an alkali metal polynaphthalenesulphonate obtained by condensation of an arylsulphonate with formaldehyde, wherein the arylsulphonate is optionally substituted on its aryl moiety by an alkyl substituent.
12. The composition according to claim 1, wherein the composition has substantially no dust, comprises substantially no organic solvent and has substantially uniform density.
13. A process for treating plants against fungal attacks, comprising the step of applying to the plants a diluted mixture obtained from mixing:
   a. water-dispersible granules consisting essentially of:
      5 to 95% of a fungicidal phosphite active substance in solid or solidified form,

0.1 to 8% of a wetting agent,
0.3 to 15% of a dispersing agent, and
0 to 50% of a support,
0 to 30% total of one or more additives selected from the group consisting of antifoaming agents, sequestering agents, stabilisers, penetrating agents, adhesives, anticaking agents and colorants,
these granules having a size of between 0.1 mm and 10 mm, and the composition has
a. a wettability time of less than 5 minutes,
b. a dispersibility of more than 92%, and
c. a suspendability of more than 86%, and
b. a diluent.

14. The process of claim 13, wherein the diluted mixture is applied from 50 to 1000 l/ha, such that the active substance is applied at 0.4 to 2 kg/ha.

15. The process of claim 13, wherein the mixture comprises substantially no organic solvent and the diluent comprises water.

* * * * *

UNITED STATES PATENT AND TRADEMARK OFFICE
CERTIFICATE OF CORRECTION

PATENT NO.    : 5,656,281
DATED         : August 12, 1997
INVENTOR(S)   : Hytte et al Claim 1, line 2, after "dispersible" insert
-- granules --.

Claim 7, line 2, delete "one of its".

Claim 8, line 3, delete "-type".

Signed and Sealed this

Twenty-first Day of October 1997

Attest:

BRUCE LEHMAN

Attesting Officer    Commissioner of Patents and Trademarks